United States Patent [19]

Bringhurst et al.

[11] Patent Number: Plant 5,267

[45] Date of Patent: Aug. 7, 1984

[54] STRAWBERRY PLANT 'FERN'

[75] Inventors: Royce S. Bringhurst, Davis; Victor Voth, Santa Ana, both of Calif.

[73] Assignee: The Regents of the University of California, Berkeley, Calif.

[21] Appl. No.: 452,700

[22] Filed: Dec. 23, 1982

[51] Int. Cl.[3] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct variety of strawberry plant of the day-neutral type primarily characterized by its early fruiting habit and ability to fruit year-round on a cyclic basis, commencing about three months after planting. The variety is a good runner producer in the summer and winter, whether rooted or not. The variety is further characterized by cymose branching with fruit occurring in clusters. The fruit is medium conic to flat wedgy and ranges internally from solid to hollow. Fruit size, durability and firmness are about the same as 'Tioga' and the variety is suitable for commercial or home garden use.

3 Drawing Figures

DESCRIPTION

This invention relates to a new and distinctive day-neutral type strawberry cultivar designated as 'Fern' which is the result of a cross between 'Tufts' (U.S. Plant Pat. No. 3,561) and Cal 69.63-103 (not patented) made in 1972. The pedigree is as follows:

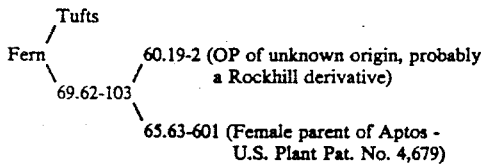

'Fern' first fruited at the University of California Wolfskill Experimental Orchards near Davis in 1973 where it was selected in 1974 and designated originally as Cal 72.8-105. It was tested later as advanced selection CN 12.

'Fern' has been propagated asexually by runners and has been tested at various University of California field stations and facilities and to a very limited extent in a few growers' fields under Test Agreement.

Figure 1:
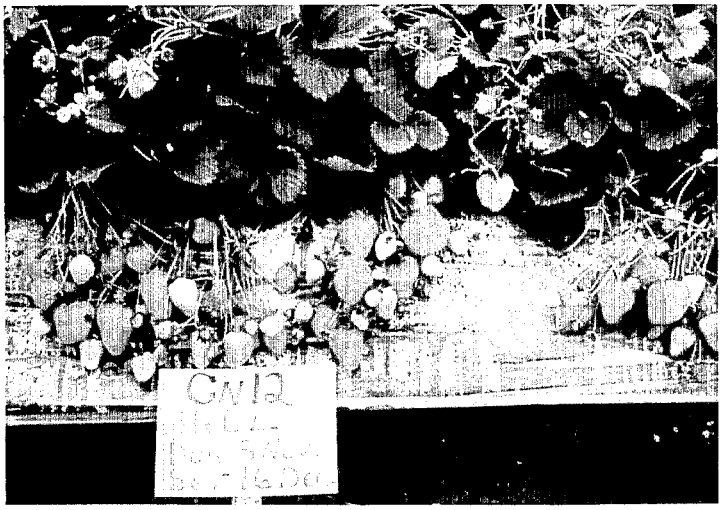
FIG. 1 shows typical growth, flowering and fruiting characteristics of the plant.
Figure 2:
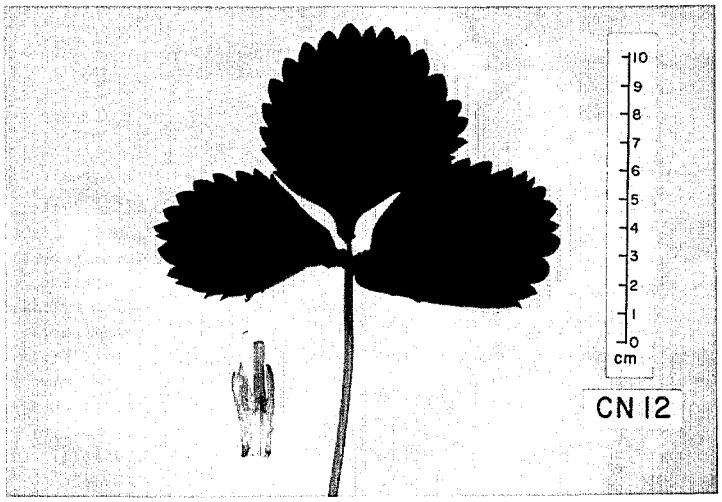
FIG. 2 shows a typical midsummer mature leaf from a plant in full fruit.
Figure 3:
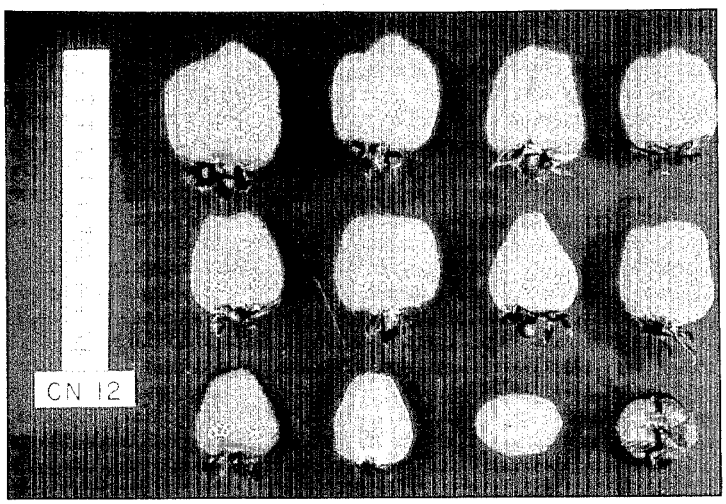
FIG. 3 shows representative early-season fruit with longitudinal and cross-sectional views.

'Fern' is early fruiting and has performed well in winter fruiting, experiments, in and outside of tunnels in southern California and in spring, summer and fall fruiting experiments in central coastal California. It is about as early as 'Hecker' (U.S. Plant Pat. No. 4,507) and the fruit quality is much better. Similar to 'Hecker', 'Fern' is strongly day-neutral and weather permitting, 'Fern' can be made to fruit year-round on a cyclic basis, commencing about three months after planting under optimum conditions.

PLANTS AND FOLIAGE

'Fern' plants are semi-erect in growth habit, more spreading than 'Hecker' and about the same size but are only about 75% as large as those of the standard 'Tioga' in both winter and summer plantings as estimated by measuring petiole length on plants in full fruit. Leaflets of 'Fern' are only about 75 to 80% as large as those of 'Tioga' with about the same number of serrations. Leaves are about the same color as those of 'Aiko', 7.5GY4/4 (Munsell Color System-Nickerson Color Fan) considerably less yellow than, but of about the same intensity as those of 'Tioga', 2.5GY4/3. Runner production in nursery plantings is very good, comparable to 'Hecker', and all of the runner plants flower within a relatively short time whether rooted or not; 'Fern' plants have a low chilling requirement, similar to 'Hecker' and will fruit in the winter under sufficiently warm growing conditions.

ISOZYMES IN LEAF EXTRACTS

'Fern' has been classified for three enzyme systems: (A) Phosphoglucoimerase (PGI); (B) Leucine amino peptidase (LAP); and (C) Phosphoglucomutase (PGM), making it identical to 'Aiko' but different from the other UC day-neutrals (below):

| | 'Tioga' | 'Aptos' & 'Brighton' | 'Hecker' | 'Fern' & 'Aiko' |
|---|---|---|---|---|
| PGI | A1 | A4 | A1 | A4 |
| LAP | B1 | B3 | B1 | B3 |
| PGM | C3 | C4 | C4 | C2 |

*1981 J. Amer. Soc. Hort. Sci 106: 684–687.

FLOWERING AND FRUITING

'Fern' is similar to California day-neutral cultivars 'Aptos', 'Brighton' and 'Hecker' in that with a minimum of conditioning, it will flower and fruit anytime, effectively independent of day length. 'Fern' flowers are borne on long, relatively thick peduncles which remain erect until brought down by the weight of the fruit. Branching is almost cymose so that the fruit of individual inflorescenses occur in clusters. The flowers are self fertile with ample pollen throughout the season and consequently there is little malformed fruit.

FRUIT APPEARANCE

'Fern' fruit is medium conic to flat wedgy. Internally fruits range from solid throughout to slightly hollow. The fruit skin color is about 5R3.5/12 (ibid), slightly darker than those of fully colored 'Pajaro' (about 5R4/12). The flesh is about the same color, almost uniform throughout with a slightly lighter ring around the core. The achenes are bright yellow to reddish positioned flush with surface to slightly exserted. The calyx is medium in size positioned from slightly embedded and slightly clasping to being borne on a short neck and reflexed. The fruit is about as firm and as durable as that of 'Tioga', 'Tufts' or 'Aiko' according to penetrometer readings and handling comparisons. The fruit size averages about as large as that of 'Tioga' with a wide range in size as the season advances because all flowers tend to set.

FRUIT QUALITY

'Fern' has averaged higher ascorbic acid content (33 mg/100 g/fr) than 'Tioga' (23) or 'Tufts' (27) but lower than 'Pajaro' (36) and 'Aiko' (41) as tested on summer and winter plantings during 1981 and 1982 by the method of Loeffler and Ponting (1942, J. Indust. and Engin. Chem. 14:846). Soluble solids readings were not significantly different from those of 'Tioga', 'Tufts', 'Douglas', 'Aiko' or 'Pajaro' from comparable plantings. The flavor of 'Fern' is excellent, comparable to that of the best flavored cultivars now used in California in our opinion and according to most who have tried it. It is suitable for fresh market and processing and for commercial usage as well as home gardening.

We claim:

1. The new and distinct variety of strawberry plant herein described and illustrated and identified by the characteristics enumerated above.

* * * * *